(12) United States Patent
Collet et al.

(10) Patent No.: US 9,988,598 B2
(45) Date of Patent: Jun. 5, 2018

(54) MULTIPLE REACTOR SYSTEM FOR CONTINUOUS GAS FERMENTATION

(71) Applicant: LanzaTech New Zealand Limited, Skokie, IL (US)

(72) Inventors: Christophe Collet, Auckland (NZ); Jan Yan Ng, Auckland (NZ); David Nathaniel Aston, Auckland (NZ)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 366 days.

(21) Appl. No.: 14/324,140

(22) Filed: Jul. 4, 2014

(65) Prior Publication Data

US 2015/0072387 A1    Mar. 12, 2015

Related U.S. Application Data

(60) Provisional application No. 61/843,046, filed on Jul. 4, 2013.

(51) Int. Cl.
| | |
|---|---|
| C12M 1/00 | (2006.01) |
| C12P 7/06 | (2006.01) |
| C12P 7/18 | (2006.01) |
| C12P 7/54 | (2006.01) |

(52) U.S. Cl.
CPC ............ *C12M 23/40* (2013.01); *C12M 23/58* (2013.01); *C12P 7/06* (2013.01); *C12P 7/18* (2013.01); *C12P 7/54* (2013.01); *Y02E 50/16* (2013.01); *Y02E 50/17* (2013.01)

(58) Field of Classification Search
CPC .......... C12M 23/58; C12M 23/40; C12P 7/06; C12P 7/54
See application file for complete search history.

(56) References Cited

U.S. PATENT DOCUMENTS

| | | | | |
|---|---|---|---|---|
| 3,591,454 | A | * | 7/1971 | Laatsch .................... C12P 7/06 426/29 |
| 5,173,429 | A | * | 12/1992 | Gaddy ...................... C12P 7/10 435/135 |
| 5,593,886 | A | | 1/1997 | Gaddy |
| 5,807,722 | A | | 9/1998 | Gaddy |
| 5,821,111 | A | | 10/1998 | Grady et al. |
| 6,136,577 | A | | 10/2000 | Gaddy |
| 6,340,581 | B1 | | 1/2002 | Gaddy |
| 6,368,819 | B1 | | 4/2002 | Gaddy et al. |
| 6,753,170 | B2 | | 6/2004 | Gaddy et al. |
| 7,078,201 | B2 | | 7/2006 | Burmaster |
| 8,143,037 | B2 | | 3/2012 | Zahn et al. |
| 8,329,456 | B2 | | 12/2012 | Tsai |
| 2011/0104770 | A1 | | 5/2011 | Tobey |
| 2012/0003705 | A1 | | 1/2012 | Jin et al. |

FOREIGN PATENT DOCUMENTS

| | | |
|---|---|---|
| EP | 117309 | 9/1984 |
| WO | 199519322 A1 | 7/1995 |
| WO | WO1998/00558 | 1/1998 |
| WO | WO2000/68407 | 11/2000 |
| WO | WO2002/08438 | 1/2002 |
| WO | WO2007/117157 | 10/2007 |
| WO | WO2008/028055 | 3/2008 |
| WO | WO2008/115080 | 9/2008 |
| WO | 2012-058508 A2 | 5/2012 |
| WO | 2012-058508 A3 | 5/2012 |
| WO | 2012-074543 A1 | 6/2012 |
| WO | 2013170863 A1 | 11/2013 |

OTHER PUBLICATIONS

Abrini, J. Naveau, H. & Nyns, E. J., Archives of Microbiology, (1994), 161, 345-351.
Hensirisak et al., Scale-up of microbubble dispersion generator for aerobic fermentation, Applied Biochemistry and Biotechnology, Oct. 2002, vol. 101, No. 3.
Klasson K. T. et al., Bioconversion of synthesis gas into liquid or gaseous fuels, Enzyme and Microbial Technology, (1992), 14, 602-608.
Klasson K. T. et al., Bioreactors for synthesis gas fermentations resources, Conservation and Recycling, (1991), 5, 145-165.
Klasson, K. T. et al., Bioreactor design for synthesis gas fermentations, Fuel, (1991), 70, 605-614.
Liou et al., International Journal of Systematic and Evolutionary Microbiology, (2005), 33, pp. 2085-2091.
Sakai et al., Biotechnology Letters, (2004), 29, pp. 1607-1612.
Svetlichny, V.A. Sokolova T.G. et al., Systematic and Applied Microbiology, (1991), 14, 254-260.
Vega, J. L. et al., Design of Bioreactors for Coal Synthesis Gas Fermentations, Resources, Conservation and Recycling, (1990), 3. 149-160.
Vega, J. L. et al., Study of Gaseous Substrate Fermentation: Carbon Monoxide Conversion to Acetate. 2. Continuous Culture. Biotech. Bioeng., (1989), 34. 6. 785-793.
Vega, J. L., et al., Study of gaseous substrate fermentations: Carbon monoxide conversion to acetate. 1. Batch culture, Biotechnology and Bioengineering, (1989), 34. 6. 774-784.

(Continued)

*Primary Examiner* — Vera Afremova
(74) *Attorney, Agent, or Firm* — Frank S Molinaro

(57) ABSTRACT

A bioreactor system is provided for continuous fermentation of a gaseous substrate, said system comprising two or more primary bioreactors and one or more secondary bioreactors connected by a central bleed line. Further provided is a process for inoculating multiple bioreactors utilizing a central bleed line, said process comprising passing fermentation broth from a first primary bioreactor to other primary bioreactors and/or secondary bioreactors via a central bleed line. Further provided is a process for maintaining stable fermentation of a gaseous substrate across multiple bioreactors, said process comprising providing fermentation broth from one or more operational primary bioreactors to one or more secondary bioreactors via a central bleed line.

10 Claims, 1 Drawing Sheet

(56) References Cited

OTHER PUBLICATIONS

PCT (PCT/NZ2014/000137) Search Report dated Nov. 11, 2014.
The Eurasian Patent Organization (EAPO) for Patent Application 201690145/31, Eurasian Patent Office, dated Aug. 10, 2017.
European Search Report for EP Patent Application 14820685.7, European Patent Office, dated Jan. 17, 2017.

* cited by examiner

MULTIPLE REACTOR SYSTEM FOR CONTINUOUS GAS FERMENTATION

CROSS-REFERENCE TO RELATED APPLICATIONS

This application is a non-provisional application under 35 U.S.C. § 111(a) and claims the benefit of priority under 35 U.S.C. § 119(e) to U.S. provisional 61/843,046 filed Jul. 4, 2013, which is hereby incorporated by reference in its entirety.

FIELD OF THE INVENTION

This invention relates to systems and processes for continuous fermentation of a gaseous substrate utilising a multiple bioreactor system. The invention provides a system wherein multiple bioreactors are connected by a central bleed line, the central bleed line allowing fluid communication between the connected bioreactors. Also provided is a process for reducing the start-up time of multiple bioreactors. Further provided is a process for flexible, continuous gas fermentation using multiple bioreactors.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feedstocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by microorganisms and therefore has the potential to contribute to GHG emissions.

Microbial fermentation of CO in the presence of $H_2$ can lead to substantially complete carbon transfer into an alcohol. However, in the absence of sufficient $H_2$, some of the CO is converted into alcohol, while a significant portion is converted to $CO_2$ as shown in the following equations:

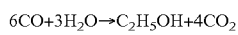

$$6CO + 3H_2O \rightarrow C_2H_5OH + 4CO_2$$

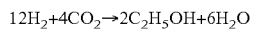

$$12H_2 + 4CO_2 \rightarrow 2C_2H_5OH + 6H_2O$$

The production of $CO_2$ represents inefficiency in overall carbon capture and if released, also has the potential to contribute to Green House Gas emissions.

WO2007/117157, the disclosure of which is incorporated herein by reference, describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process. WO2008/115080, the disclosure of which is incorporated herein by reference, describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products.

U.S. Pat. No. 7,078,201 and WO 02/08438 also describe improving fermentation processes for producing ethanol by varying conditions (e.g. pH and redox potential) of the liquid nutrient medium in which the fermentation is performed. As disclosed in those publications, similar processes may be used to produce other alcohols, such as butanol.

Even minor improvements to a fermentation process for producing one or more acids and/or one or more alcohols can have a significant impact on the efficiency, and more particularly, the commercial viability, of such a process. It is an object of the present invention to provide system(s) and/or method(s) that overcomes disadvantages known in the art and provides the public with new methods for the optimal production of a variety of useful products.

SUMMARY OF THE INVENTION

In a first aspect, there is provided a bioreactor system for continuous fermentation, comprising:
 a. two or more primary bioreactors adapted for fermentation of a gaseous substrate by one or more microorganisms to produce a fermentation broth;
 b. one or more secondary bioreactor adapted for fermentation of a gaseous substrate by one or more microorganisms to produce one or more products; and
 c. a central bleed line,
wherein at least two of the primary bioreactors of the system are capable of fluid communication with each other and fluid communication with at least one secondary bioreactor via the central bleed line.

In one embodiment at least a portion of one or more acids produced in the fermentation broth of the primary bioreactors is converted to its corresponding alcohol in the one or more secondary bioreactor(s).

In one embodiment of the first aspect, all bioreactors are configured for fermentation of a gaseous substrate to produce products including acid(s) and/or alcohol(s). In a particular embodiment, the gaseous substrate is selected from the group consisting of CO, $H_2$, $CO_2$ and mixtures thereof. In a particular embodiment, the gaseous substrate comprises CO and optionally $H_2$. In an alternative embodiment, the gaseous substrate comprises $CO_2$ and $H_2$.

In one embodiment of the invention, the primary bioreactors comprise an outlet conduit for passing fermentation broth to the central bleed line. In certain aspects, the primary bioreactors and secondary bioreactors comprise an inlet conduit for receiving fermentation broth from the central bleed line. In particular embodiments, fluid communication between bioreactors connected to the central bleed line is controlled by valves (also referred to as inoculation valves) integrated with the inlet conduits. These valves control the passage of fermentation broth from a primary bioreactor to other primary bioreactors and/or secondary bioreactors depending on whether they are opened or closed by an operator.

In a particular embodiment, the primary bioreactors are operated at conditions to primarily promote growth of one or more microorganisms and to produce one or more products. In a particular embodiment, the secondary bioreactors are primarily operated at conditions to produce one or more products from a gaseous substrate In one embodiment the fermentation broth produced in the primary reactor is passed to a secondary bioreactor via a central bleed line, and at least a portion of one or more acids in the fermentation broth passed from the primary bioreactor to a secondary bioreactor is converted to its corresponding alcohol in the secondary bioreactor.

In one embodiment of the first aspect, the bioreactor system comprises at least two primary bioreactors and at least one secondary bioreactor, wherein all bioreactors are connected via the central bleed line. In a particular embodiment, the system comprises between 2-16 primary bioreactors and between 1-16 secondary bioreactors. In a further embodiment, the system comprises between 2-8 primary bioreactors and between 1-8 secondary bioreactors. In a preferred embodiment, the system comprises 4 primary bioreactors and 4 secondary bioreactors.

In one embodiment of the first aspect, a central bleed line is connected to all bioreactors of the system and allows fluid communication between all of the primary bioreactors and/or all of the secondary bioreactors. In one embodiment, a central bleed line provides fermentation broth from at least one of the primary bioreactors to at least one of the secondary bioreactors. In a particular embodiment, each primary bioreactor feeds one corresponding secondary bioreactor via the central bleed line. In operation, the bioreactors are run in separate trains of primary bioreactors and corresponding secondary bioreactors via the central bleed line, wherein at least a portion of the fermentation broth from any given primary bioreactor is provided to secondary bioreactors via the central bleed line. In an alternative embodiment, all primary bioreactors feed all secondary bioreactors fermentation broth on a time share configuration via the central bleed line, wherein the passage of fermentation broth into any given secondary bioreactors is controlled by valves integrated with the inlet conduits of the secondary bioreactors In particular embodiments, during steady state fermentation, fermentation broth will be continuously provided from the primary bioreactors to the secondary bioreactors via the central bleed line. Fermentation broth comprising at least one fermentation product will be continuously removed from both the primary and secondary bioreactors. In a particular embodiment, additional media is fed to the primary bioreactors and secondary bioreactors such that a substantially constant volume of fermentation broth is maintained in all bioreactors of the system. In a particular embodiment, the rate at which products are produced is substantially the same in both the primary and secondary bioreactors. However, in preferred embodiments, the rate at which products are produced is substantially greater in the secondary bioreactors than in the primary bioreactors.

In one embodiment, the central bleed line provides fermentation broth from at least one of the primary bioreactors to at least one other primary bioreactor. In this configuration, the fermentation broth from one primary bioreactor is used to inoculate at least one other primary bioreactor. In a particular embodiment, a first primary bioreactor is inoculated by an inoculator which, once operational, passes at least a portion of the fermentation broth to at least one other primary bioreactor via the central bleed line. The central bleed line is utilised to pass at least a portion of fermentation broth from one operational primary bioreactor to multiple non-operational primary bioreactors at the same time and/or individual non-operational primary bioreactors so that each is established in series. In a preferred embodiment, the central bleed line is utilised to pass a portion of fermentation broth from an operational primary bioreactor to multiple non-operational primary bioreactors at the same time in order to reduce the overall start up time of the system.

In a further embodiment, at least one operational primary bioreactor passes fermentation broth to at least one non-operational secondary bioreactor via the central bleed line. In this configuration, the fermentation broth from the operational primary bioreactor(s) is used to inoculate one or substantially all of the secondary bioreactors in the system. In a particular embodiment, the secondary bioreactors are individually passed fermentation broth from the primary bioreactors via the central bleed line prior to completion of inoculation of substantially all primary bioreactors in the system. In an alternative embodiment, all secondary bioreactors are passed fermentation broth from the primary bioreactors at the same time via the central bleed line once all primary bioreactors in the system have been inoculated.

In a particular embodiment, the primary and/or secondary bioreactors are used for the fermentation of gaseous substrates selected from the group consisting of CO, $CO_2$, $H_2$ and mixtures thereof to produce products including ethanol, acetic acid, 2,3-butanediol, butanol, iso-propanol, lactate, succinate, methyl ethyl ketone (MEK), propanediol, 2-propanol, acetoin, iso-butanol, citramalate, butadiene, poly lactic acid, isobutylene, 3-hydroxy propionate (3HP), acetone and fatty acids. Typically, the microbial fermentation of such substrates is carried out in liquid nutrient media by carboxydotrophic bacteria. In certain embodiments the carboxydotrophic bacteria is selected from the genus *Clostridium*. In further embodiments the carboxydotrophic bacteria is selected from the group consisting of *Clostridium autoethanogenum, Clostridium ljungdahli, Clostridium ragsdalei* and, *Clostridium carboxydivorans*. In particular embodiments, the fermentation is conducted by micro-organisms suspended in the liquid nutrient media.

In one embodiment at least a portion of one or more acid products produced in a primary bioreactor is converted to its corresponding alcohol in a secondary bioreactor. In a particular embodiment at least a portion of acetic acid produced in at least one primary reactor is converted to ethanol in the secondary bioreactor(s).

In a second aspect, there is provided a process for inoculating multiple bioreactors utilising a central bleed line, the process comprising:
a. supplying a gaseous substrate to a first primary bioreactor comprising a liquid nutrient media;
b. inoculating the first primary bioreactor with one or more microorganisms;
c. fermenting the gaseous substrate to produce a fermentation broth comprising one or more microorganisms and one or more products;
d. passing at least a portion of the fermentation broth from the first primary bioreactor to inoculate one or more other primary bioreactors via a central bleed line;
e. operating the at least one other primary bioreactor at conditions to primarily promote microbial growth; and
f. passing at least a portion of the fermentation broth from one or more primary bioreactors to inoculate one or more secondary bioreactors via the central bleed line.

In a third aspect, there is provided a process for maintaining steady state fermentation of a gaseous substrate across multiple bioreactors, comprising:
a. supplying a gaseous substrate to two or more primary bioreactors comprising a liquid nutrient media containing one or more microorganisms;
b. fermenting the gaseous substrate in the two or more primary bioreactors to produce a fermentation broth comprising one or more microorganisms and one or more products;
c. passing at least a portion of the fermentation broth from one primary bioreactor to one or more secondary bioreactors via a central bleed line; and
d. determining whether one or more of the primary bioreactors of (c) is operational or not, wherein if one or more of the primary bioreactor is non-operational, at least a portion of fermentation broth from one or more operational primary bioreactors is provided to the one or more secondary bioreactors of (c) via the central bleed line.

In particular embodiments of the second and third aspects, the processes are employed in the system as described in the first aspect. In particular embodiments, the processes are employed in a multiple bioreactor system configured for continuous gas fermentation comprising two or more bioreactors in fluid communication via a central bleed line. In a preferred embodiment, the system comprises 4 primary bioreactors and 4 secondary bioreactors all in fluid connection via a central bleed line.

In one embodiment, one or more primary bioreactors and/or secondary bioreactors are inoculated using fermentation broth provided via a central bleed line from one or more operational primary bioreactors. In a particular embodiment, each non-operational primary bioreactor is inoculated from an operational primary bioreactor in series, wherein fermentation broth from an operational primary bioreactor is provided to a subsequent non-operational primary bioreactor via a central bleed line. In a preferred embodiment, one or more operational primary bioreactors are used to simultaneously inoculate multiple non-operational primary bioreactors, wherein fermentation broth from the one or more primary bioreactors is passed to multiple non-operational primary bioreactors at substantially the same time via a central bleed line.

In a particular embodiment, one or more secondary bioreactors are inoculated from fermentation broth provided via a central bleed line from at least one operational primary bioreactor. In a particular embodiment, one or more secondary bioreactors are inoculated from fermentation broth provided via a central bleed line, wherein the fermentation broth is combined from multiple primary bioreactors.

In one embodiment, the bioreactors are run in separate trains of primary bioreactors and corresponding secondary bioreactors via a central bleed line, wherein at least a portion of the fermentation broth from any given primary bioreactor is provided to secondary bioreactors via a central bleed line. In the event that one of the primary bioreactor's fermentation broth collapses (i.e., a primary reactor becomes non-operational) and the primary bioreactor can no longer supply an adequate amount of fermentation broth to its corresponding secondary bioreactor, the secondary bioreactor is provided an adequate amount of fermentation broth from at least one of the remaining primary bioreactors via a central bleed line. In a particular embodiment, the corresponding secondary bioreactor is provided an adequate amount of fermentation broth from all remaining primary bioreactors. In a particular embodiment, the liquid nutrient media level in one or more remaining primary bioreactors and/or secondary bioreactors is substantially increased in order for substantially the same amount of gas to be utilised as before one of the primary bioreactors became non-operational. The primary bioreactor that is non-operational is then restarted from at least a portion of the additional fermentation broth available in the one or more remaining primary bioreactors, provided to the non-operational primary bioreactor via a central bleed line.

In the event that a secondary bioreactor becomes non-operational, one or more operational secondary bioreactors in the system are provided fermentation broth from one or more of the operational primary bioreactors via a central bleed line. In a particular embodiment, the liquid nutrient media level in one or more of both the operational primary bioreactors and operational secondary bioreactors is substantially increased in order for substantially the same amount of gas to be utilised as before one of the secondary bioreactors became non-operational. The non-operational secondary bioreactor is then reinoculated from at least a portion of the surplus fermentation broth available in the one or more operational primary bioreactors and/or operational secondary bioreactors, provided to the non-operational secondary bioreactor via a central bleed line.

In the event that the gas supply to the primary bioreactors and/or secondary bioreactors becomes limited, at least one of the primary bioreactors and/or the secondary bioreactors may be temporarily shut down. In a particular embodiment, more primary bioreactors than secondary bioreactors remain operational. In a particular embodiment, the liquid nutrient media level in one or more of the operational primary bioreactors and/or operational secondary bioreactors is increased. Once gas supply has returned to substantially normal levels, the bioreactors that have been shut down (non-operational) are reinoculated from at least a portion of the surplus fermentation broth available in the one or more operational primary bioreactors and/or operational secondary bioreactors, via a central bleed line.

In various embodiments, the fermentation is carried out using a microorganism culture comprising one or more strains of carboxydotrophic bacteria. In various embodiments, the carboxydotrophic bacterium is selected from *Clostridium, Moorella, Oxobacter, Peptostreptococcus, Acetobacterium, Eubacterium,* or *Butyribacterium*. In one embodiment, the carboxydotrophic bacterium is *Clostridium autoethanogenum*. In a particular embodiment, the bacterium has the identifying characteristics of the bacterium deposited at the German Resource Centre for Biological Material (DSMZ) Inhoffenstraβe 7 B, 38124 Braunschweig, Germany, under the accession number DSMZ10061 or DSMZ23693.

The gaseous substrate may comprise a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. Alternatively, the gaseous substrate is a reformed gas from sources including natural gas, shale gas, associated petroleum gas and biogas. In one embodiment of the invention, the gaseous substrate is syngas. In one embodiment, the gaseous substrate comprises a gas obtained from a steel mill.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

The invention will now be described in detail with reference to the accompanying Figures in which.

DETAILED DESCRIPTION OF THE INVENTION

Definitions

Figure 1:
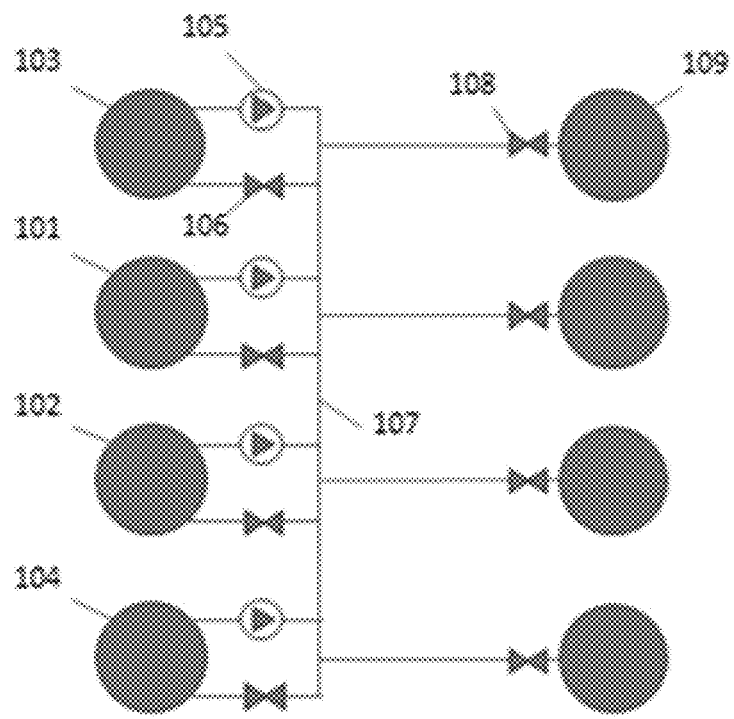
FIG. 1 shows an embodiment of the multiple bioreactor system, wherein during normal operation each primary bioreactor provides fermentation broth to one corresponding secondary bioreactor via a central bleed line.

Unless otherwise defined, the following terms as used throughout this specification are defined as follows:

The term "bioreactor" and/or "reactor" includes any fermentation device consisting of one or more vessels and/or towers or piping arrangements, such as an immobilised cell reactor, a gas-lift reactor, a bubble column reactor (BCR), a circulated loop reactor, a membrane reactor, such as a Hollow Fibre Membrane Bioreactor (HFM BR) or a trickle bed reactor (TBR).

The term "central bleed line" comprises a line, tube, channel or conduit that is connected to all bioreactors in a multiple bioreactor system, and which allows for a portion of fermentation broth to pass from at least one bioreactor in the system to at least one other bioreactor in the system. Preferably, the fermentation broth removed from the bioreactor has not been passed to a separator prior to being provided to the central bleed line.

The term "trains", "reactor trains" and the like is intended to encompass a system wherein a primary bioreactor is connected to at least one secondary bioreactor. In particular embodiments, the reactor train comprises a third or fourth bioreactor connected to the train. The term includes systems where a plurality of primary reactors is connected to a plurality of secondary or tertiary reactors.

The term "gaseous substrate" includes any gas which contains a compound or element used by a microorganism as a carbon source and optionally energy source in fermentation. The gaseous substrate will typically contain a significant proportion of CO, preferably at least 5% to 100% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises 30% or less $H_2$ by volume, 20% or less $H_2$ by volume, 15% or less $H_2$ by volume or 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as 1% to 80% $CO_2$ by volume, or 1% to 30% $CO_2$ by volume. In one embodiment the substrate comprises less than or equal to 20% $CO_2$ by volume. In particular embodiments the substrate comprises less than or equal to 15% $CO_2$ by volume, less than or equal to 10% $CO_2$ by volume, less than or equal to 5% $CO_2$ by volume or substantially no $CO_2$.

The term "liquid nutrient media" includes a liquid medium comprising nutrients suitable for fermentation using one or more microorganisms. The liquid nutrient media will contain vitamins and/or minerals sufficient to permit growth of the micro-organism(s) used. Anaerobic media suitable for fermentation using CO are known in the art. For example, suitable media are described in Beibel (2001).

The term "product" as used herein is intended to encompass substances produced by the microbial fermentation.

Product can include alcohols, acids or other chemicals. Products can also include gases produced by the microbial fermentation process.

Unless the context requires otherwise, the phrases "fermenting", "fermentation process" or "fermentation reaction" and the like, as used herein, are intended to encompass both the growth phase and product biosynthesis phase of the process.

The terms "operational", "normal operation", "stable fermentation" and the like refer to a situation wherein the culture of one or more microorganisms within a bioreactor, or within a train of two or more reactors, are in a growth phase and/or product biosynthesis phase of the fermentation process. Conversely, the term "non-operational" refers to a situation wherein the culture of one or more microorganisms within a reactor, or within a train of two or more bioreactors, has died, or a situation in which the fermentation process is no longer occurring within the reactor to the point at which products can be recovered.

The term "gas limited", or "limited" when used in relation to a gaseous substrate, is intended to encompass a situation in which a gaseous substrate is supplied to one or more bioreactors in a quantity that is below the optimum (or maximum) amount of substrate which the microorganism can uptake.

The term "fluid communication" is intended encompass a situation wherein a liquid is passed between two or more bioreactors via a bleed line. In particular embodiments, the liquid passed between two or more bioreactors is a fermentation broth. In certain embodiments the liquid is a permeate stream or a cell-depleted stream. In certain embodiments the liquid stream passes through a treatment zone prior to entering the central bleed line. A skilled person would understand that a treatment zone can include any number of treatment stages, including but not limited to the removal of biomass, removal of proteins, separation of and removal of at least a portion of the product stream, addition of further nutrients or water.

While the following description focuses on particular embodiments of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce ethanol, acetic acid, 2,3-butanediol, butanol, iso-propanol, lactate, succinate, methyl ethyl ketone (MEK), propanediol, 2-propanol, acetoin, iso-butanol, citramalate, butadiene, poly lactic acid, isobutylene, 3-hydroxy propionate (3HP), acetone and fatty acids. The methods may also be of use in producing hydrogen. By way of example, these products may be produced by fermentation using microbes from the genus *Moorella, Clostridia, Ruminococcus, Acetobacterium, Eubacterium, Butyribacterium, Oxobacter, Methanosarcina* and *Desulfotomaculum*.

The inventors have devised a multiple bioreactor system that allows for continuous fermentation of a gaseous substrate. The system comprises multiple bioreactors linked by a central bleed line, wherein the bleed line allows for fluid communication of a fermentation broth between the multiple bioreactors of the system. Gas fermentation systems are known in the art, although such systems typically involve a batch process. Continuous gas fermentation systems are also known, although these involve single bioreactors or independent trains of up to two linked bioreactors. Such processes are known to take a significant amount of time to initially start up and are inflexible in the event that one of the two bioreactors becomes non-operational (i.e., a culture collapse). In the event of such a collapse in one bioreactor, the entire process must be restarted, resulting in significant downtime. A surprising advantage of linking multiple bioreactors to a central bleed line is that it allows substantially faster start-up/inoculation of multiple bioreactors and greater flexibility during operation. The central bleed line allows for a single bioreactor to inoculate a plurality of other linked bioreactors, instead of individually inoculating each bioreactor in the system from an inoculator. The central bleed line also allows for multiple bioreactors to compensate for the loss of any given bioreactor in the system by providing fermentation broth via the central bleed line to linked bioreactors that would have otherwise also become non-operational if in an independent train configuration. The uptime of the system is therefore maximised by the flexibility provided by the central bleed line.

The system of the invention comprises a plurality of primary bioreactors and secondary bioreactors, wherein all bioreactors are in fluid communication via a central bleed line. In particular embodiments, gaseous substrate is provided to both the primary and secondary bioreactors of the system. In particular embodiments, the primary bioreactors are operated under conditions to primarily utilise a gaseous substrate to promote growth of one or more microorganisms and to produce one or more products. In a particular embodiment, the secondary bioreactors are operated under conditions to produce one or more products from a gaseous substrate of the primary bioreactors. In certain embodiments at least a portion of fermentation broth is passed from a primary bioreactor to at least one secondary bioreactor, and at least a portion of one or more acids in the fermentation broth is converted to its corresponding alcohol in a secondary bioreactor. In such a configuration, the primary bioreactor provides a portion of fermentation broth comprising one or more microorganisms and/or one or more products to the central bleed line. This fermentation broth is then passed to one or more secondary bioreactors via the central bleed line. Fluid communication between bioreactors connected to the central bleed line is controlled by valves/inoculation valves integrated with the inlet conduits of the bioreactors. These valves control the passage of fermentation broth from a primary bioreactor to other primary bioreactors and/or secondary bioreactors depending on whether they are opened or closed by an operator.

During normal operation, the bioreactors are run in separate trains of primary bioreactors and corresponding secondary bioreactors in fluid communication via the central bleed line. This train configuration allows for continuous fermentation and, in particular embodiments, allows for higher product titres as the fermentation broth provided from the primary bioreactors contains one or more acids.

In certain embodiments, the fermentation broth is removed from the primary bioreactors by a bleed pump. The level of broth in the primary bioreactors is kept constant by continuous broth removal by the bleed pump to the central bleed line and a constant supply of additional liquid nutrient media. Additional liquid nutrient media may also be introduced to the secondary bioreactors and fermentation broth is removed as either a permeate stream or separate bleed stream in order to keep the broth level constant.

In particular embodiments, a portion of the fermentation broth from the primary bioreactor is passed directly to the secondary bioreactor via the central bleed line. However, in certain embodiments, the fermentation broth is treated either prior to being passed to the central bleed line or before to being provided to the secondary bioreactor. Treatment may comprise the addition of nutrients, metals and B-vitamins to the fermentation broth and/or removal of biomass, products, acids, organic molecules and/or inorganic molecules.

In embodiments of the invention, the system has application in the fermentation of gaseous substrates to one or more products, said products including acids, alcohols and diols. In particular, ethanol, acetic acid and 2,3-butanediol are produced by fermentation of a gaseous substrate comprising CO.

The system may be comprised of any number of primary bioreactors and secondary bioreactors. In particular embodiments, the multiple bioreactor system comprises at least two primary bioreactors and at least one secondary bioreactor, wherein all bioreactors are connected via a central bleed line. In particular embodiments, the system comprises between 2-16 primary bioreactors and between 1-16 secondary bioreactors. In further embodiments, the system comprises between 2-8 primary bioreactors and between 1-8 secondary bioreactors. However, in preferred embodiments, the system comprises 4 primary bioreactors and 4 secondary bioreactors.

The bioreactors of the system may be any suitable for fermentation, such as an immobilised cell reactor, a gas-lift reactor, a bubble column reactor (BCR), a membrane reactor, such as a Hollow Fibre Membrane Bioreactor (HFM BR) or a trickle bed reactor (TBR). The bioreactors may be of any size suitable for a desired volume of production. In particular embodiments, the secondary bioreactors are substantially larger than the primary reactors. Alternatively, all bioreactors may be substantially the same size. Typically, the gaseous substrate is introduced to the bioreactors via a gas inlet port. The gaseous substrate can be sparged into bioreactor by any known sparging means. However, in particular embodiments, the gas is introduced through one or more fine bubble spargers or diffusers. Gas that is not utilised by microorganisms contained within the reactor, or gas produced as a by-product by the microorganisms during the fermentation reaction, exits the reactor through a gas outlet port.

In particular embodiments, the bioreactors of the system comprise an outlet conduit for passing fermentation broth to the central bleed line, and an inlet conduit for receiving fermentation broth from the central bleed line. Products produced within the bioreactors are removed via a permeate stream conduit, which passes fermentation broth containing products to a recovery zone as a permeate stream. In particular embodiments, the permeate stream is integrated with a cell recycle system. The cell recycle system provides a means to separate microorganisms from permeate in order that the microorganisms are returned to the reactor for further fermentation. A cell recycle module continuously draws broth permeate, while retaining cells. Those skilled in the art would understand that cell recycle members may include, but are not limited to, cell recycle membranes or disc-stack centrifugal separators.

A surprising advantage of the present invention is that the central bleed line allows for different dilution rates between the primary bioreactors and secondary bioreactors during operation. This also allows for varying numbers of primary and secondary bioreactors in the system. In embodiments where there are the same number of primary bioreactors and secondary bioreactors, the dilution rates are substantially the same. In embodiments where there are more secondary bioreactors than there are primary bioreactors, the dilution rate is substantially lower in the secondary bioreactors in order to increase the residence time of the microorganism in the secondary bioreactor.

While it is preferred that the multiple bioreactor system and the processes described herein are applied to gas fermentation, it will be appreciated that the system and/or processes may be used for alternative fermentation processes utilising multiple reactors.

Various embodiments of systems and processes of the invention are described in the accompanying Figures. While the following embodiments are directed to fermentation systems with 4 primary bioreactors and 4 secondary bioreactors, any number of primary and secondary bioreactors may be utilised in the system.

In the following description of both FIGS. 1 and 2, all bleed pumps of the system are referred to as 105 and all inoculation valves of the system are referred to as 106. Similarly, all secondary bioreactors of the system are referred to as 109.

FIG. 1 is a diagram of a multiple bioreactor system connected by a central bleed line 107. At start up, primary bioreactor 101 is inoculated from an inoculator while being fed gaseous substrate and liquid nutrient media. Once primary bioreactor 101 is operational, the bleed pump 105 passes the fermentation broth from primary bioreactor 101 to the central bleed line 107. The inoculation valve 106 of primary bioreactor 102 is then opened, providing fermentation broth for inoculation. The same process is used to inoculate primary bioreactor 103 from primary bioreactor 101 once it is operational, and similarly primary bioreactor 104 from primary bioreactor 102. In an alternative embodiment, once primary bioreactor 101 is operational it continuously bleeds fermentation broth to the central bleed line 107, which is provided to all of primary bioreactors 102-104 at the same time.

Once all primary bioreactors 101-104 are operational, the bleed valve 108 is opened and a portion of fermentation broth from the primary bioreactors 101-104 is passed through the central bleed line 107 to the secondary bioreactors 109 for inoculation. In certain embodiments, a portion of fermentation broth is passed via the central bleed line 107 from the established primary bioreactors 101-104 to individual secondary bioreactors 109 for inoculation. In alternative embodiments, the fermentation broth from the primary bioreactors 101-104 is continuously bled via the central bleed line 107 to all secondary bioreactors at the same time for inoculation.

In operation, the primary bioreactors 101-104 ferment a gaseous substrate to produce one or more products as described herein. In particular embodiments, the primary bioreactors 101-104 are configured to substantially promote growth of one or more microorganisms and to produce one or more products. Fermentation broth comprising one or more microorganisms and/or one or more products is removed from one or more of the primary bioreactors 101-104 by the bleed pump 105 and passed through the central bleed line 107 to at least one of the secondary bioreactors 109. In particular embodiments, one primary bioreactor, e.g., primary bioreactor 101, provides fermentation broth to one corresponding secondary bioreactor 109 via the central bleed line 107 in normal operation. In particular embodiments, the secondary bioreactors 109 are operated at conditions to produce one or more products from a gaseous substrate. In particular embodiments at least a portion of the one or more acid products in the fermentation broth received from a primary bioreactor is converted to its corresponding acid.

In the event that one of the primary bioreactors becomes non-operational, for example the fermentation broth of primary bioreactor 101 collapses and primary bioreactor 101 can no longer supply an adequate amount of broth to allow corresponding secondary bioreactor 109 to remain operational, the secondary bioreactor 109 is provided an adequate amount of fermentation broth for operation from at least one of the remaining primary bioreactors, for example primary bioreactors 102-104, via the central bleed line 107. In particular embodiments, the corresponding secondary bioreactor 109 is provided an adequate amount of fermentation broth from all remaining primary bioreactors 102-104. The fermentation broth level in the remaining primary bioreactors 102-104 and secondary bioreactors 109 is substantially increased in order for substantially the same amount of gas to be utilised as before primary reactor 101 became non-operational. Primary bioreactor 101 is then reinoculated from at least a portion of the additional fermentation broth available in primary bioreactors 102-104, provided to primary bioreactor 101 via the central bleed line.

In the event that one of the secondary bioreactors 109 becomes non-operational, one or more remaining secondary bioreactors 109 in the system are provided fermentation broth from one or more of the primary bioreactors 101-104 via the central bleed line 107. In a particular embodiment, the fermentation broth level in one or more of the primary bioreactors 101-104 and remaining secondary bioreactors 109 is substantially increased in order for substantially the same amount of gas to be utilised as before one of the secondary bioreactors 109 became non-operational. The secondary bioreactor 109 that has gone down is then restarted from at least a portion of the additional fermentation broth available in the one or more primary bioreactors 101-104 and/or remaining secondary bioreactors 109, provided to the down secondary bioreactor 109 via the central bleed line 107.

In the event that the gas supply to the primary bioreactors 101-104 becomes limited, at least one of the primary bioreactors 101-104 and/or the secondary bioreactors 109 may be temporarily shut down. In particular embodiments, substantially more primary bioreactors 101-104 than secondary bioreactors 109 remain operating. In particular embodiments, the fermentation broth level in one or more of the remaining primary bioreactors 101-104 and/or remaining secondary bioreactors 109 is increased. Once gas supply has returned to normal level, any bioreactors that have been shut down are reinoculated from at least a portion of the additional fermentation broth available in the one or more remaining primary bioreactors 101-104 and/or remaining secondary bioreactors 109, wherein the additional fermentation broth is provided to the non-operational bioreactors via the central bleed line 107.

Figure 2:
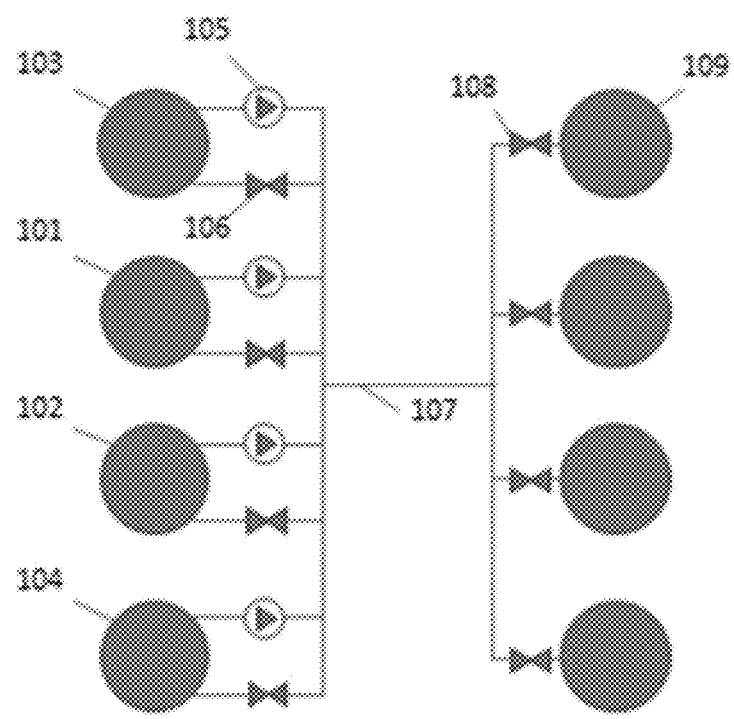
FIG. 2 shows an alternative embodiment of the multiple bioreactor system, wherein during normal operation all primary bioreactors provide fermentation broth to all secondary bioreactors via a central bleed line.

FIG. 2 is a diagram of an alternative multiple bioreactor system connected by a central bleed line 107. The process for inoculation, operation, primary/secondary bioreactor collapse, and limited gas supply are substantially the same as those described above for FIG. 1. However, the design of the central bleed line 107 in FIG. 2 allows for the fermentation broth from all primary bioreactors 101-104 to be combined and passed to the secondary bioreactors 109 via the central bleed line 107. The fermentation broth passing through the central bleed line 107 may be equally distributed to all secondary bioreactors 109, or provided to one secondary bioreactor 109 at a time on a time share configuration. In a time share configuration, each secondary bioreactor 109 may ferment the received fermentation broth in a batch process.

Fermentation

Processes for the production of ethanol and other alcohols from gaseous substrates (such as those described in the background section above) are known. Exemplary processes include those described for example in WO 2007/117157 and WO 2008/115080, as well as U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al., Archives of Microbiology 161: pp 345-351). Other suitable bacteria include those of the genus *Moorella*, including *Moorella* sp HUC22-1 (Sakai et al., Biotechnology Letters 29: pp 1607-1612), and those of the genus *Carboxydothermus* (Svetlichny, V. A., et al. (1991), Systematic and Applied Microbiology 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

In one embodiment, the microorganism is selected from the group of carboxydotrophic *Clostridia* comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*. In a further embodiment, the microorganism is from the cluster of carboxydotrophic *Clostridia* comprising the species *C. autoethanogenum*, *C. ljungdahlii*, and *C. ragsdalei* and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593, 886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11$^T$ (ATCC BAA-622) (WO 2008/028055), related isolates such as "*C. coskatii*" (US20110229947) and "*Clostridium* sp." (Tyurin & Kiriukhin, 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of the above-referenced cluster have a similar morphology and size (logarithmic growing cells are between 0.5-0.7×3-5 µm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini et al., 1994; Köpke et al., 2011; Tanner et al., 1993) (WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al., 2011). Also reduction of carboxylic acids into their corresponding alcohols has been shown in a range of these organisms (Perez, Richter, Loftus, & Angenent, 2012). These traits are therefore not specific to one organism like *C. autoethanogenum* or *C. ljungdahlii*, but rather general traits for carboxydotrophic, ethanol-synthesizing *Clostridia* and it can be anticipated that mechanism work similar across these strains, although there may be differences in performance (Perez et al., 2012).

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061. In a further embodiment, the *Clostridium autoethanogenum* is a *Clostridium autoethanogenum* having the identifying characteristics of DSMZ deposit number DSMZ 23693.

The fermentation may be carried out in any suitable bioreactor. In some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as is conducted in a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. In alternative embodiments, the CO-containing gas is a purpose-reformed gas from sources including natural gas, shale gas, associated petroleum gas and biogas. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

The CO-containing gaseous substrate will ideally contain a significant proportion of CO, such as at least 5% to 100% CO by volume, or from 20% to 95% CO by volume, or from 40% to 95% CO by volume, or from 60% to 90% CO by volume or from 70% to 90% CO by volume. Gaseous substrates having lower concentrations of CO, such as 6%, may also be appropriate, particularly when $H_2$ and $CO_2$ are also present.

While it is not necessary for the gaseous substrate to contain any hydrogen, the presence of hydrogen will generally not be detrimental to product formation in accordance with methods of the invention. However, in certain embodiments of the invention, the gaseous substrate is substantially hydrogen free (less than 1%). The gaseous substrate may also contain some $CO_2$, such as 1% to 30% by volume, or such as 5% to 10% $CO_2$.

As noted previously, the presence of hydrogen in the substrate stream can lead to an improvement in efficiency of overall carbon capture and/or ethanol productivity. For example, WO0208438 describes the production of ethanol using gas streams of various compositions. In one preferred embodiment, a substrate stream comprising 63% H2, 32% CO and 5% $CH_4$ was provided to a culture of *C. ljungdahlii* in a bioreactor to promote microbial growth and ethanol production. When the culture reached a steady state and microbial growth was no longer the main objective, the substrate stream was switched to 15.8% $H_2$, 36.5% CO, 38.4% $N_2$ and 9.3% $CO_2$ in order to provide CO in a slight excess and promote ethanol production. This document also describes gas streams with higher and lower CO and $H_2$ concentrations.

Accordingly, it may be necessary to alter the composition of the substrate stream in order to improve alcohol production and/or overall carbon capture. Additionally or alternatively, the composition may be altered (i.e. CO, $CO_2$ and/or $H_2$ levels adjusted) to optimise the efficiency of the fermentation reaction and ultimately improve alcohol production and/or overall carbon capture.

In some embodiments, the CO-containing gaseous substrate may be sourced from the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e. partially combusted with oxygen, to produce synthesis gas (syngas comprising significant amounts of $H_2$ and CO). Gasification processes typically produce a synthesis gas with a molar ratio of $H_2$ to CO of 0.4:1 to 1.2:1, together with lesser amounts of $CO_2$, $H_2S$, methane and other inert substances. The ratio of the gas produced can be varied by means known in the art and are described in detail in WO200701616. However, by way of example, the following gasifier conditions can be altered to adjust the $CO:H_2$ product ratio: feedstock composition (particularly C:H ratio), operating pressure, temperature profile (influencing quench of product mix) and oxidant employed (air, oxygen enriched air, pure $O_2$ or steam; wherein steam tends to result in higher $CO:H_2$ ratios). Accordingly, the operating conditions of the gasifier can be adjusted to provide a substrate stream with a desirable composition for fermentation or blending with one or more other streams to provide an optimised or desirable composition for increased alcohol productivity and/or overall carbon capture in a fermentation process.

In other embodiments, the substrate comprising CO can be derived from the steam reforming of hydrocarbons. Hydrocarbons, such as natural gas hydrocarbons can be reformed at high temperature to yield CO and $H_2$ according to the following:

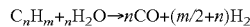

$$C_nH_m + nH_2O \rightarrow nCO + (m/2+n)H_2$$

By way of example, steam methane reforming involves reacting steam with methane to produce CO and $H_2$ at elevated temperature (700-1100° C.) in the presence of a nickel catalyst. The resulting stream (comprising 1 mol CO and 3 mol $H_2$ for every mol $CH_4$ converted) can be passed directly to the fermenter or blended with a substrate stream from another source to increase ethanol productivity and/or overall carbon capture in a fermentation process. Alcohols such as methanol can also be reformed to produce $CO_2$ and $H_2$ that may be used in a similar manner.

In another embodiment, the substrate comprising CO is derived from the steel manufacturing process. In the steel making process, iron ore is crushed and pulverised, subjected to pre-treatments such as sintering or pelletizing, and then passed to a blast furnace (BF), where it is smelted. In the smelting process, coke serves as the source of carbon, which works as a reducing agent to reduce the iron ore. Coke acts as the heat source for heating and melting the materials. The hot metal is decarburised in a basic oxygen furnace (BOF) by injecting a high-velocity jet of pure oxygen against the surface of the hot metal. The oxygen reacts directly with carbon in the hot metal to produce carbon monoxide (CO). Thus, a gas stream with a high CO content is exhausted from the BOF. According to certain embodiments of the invention, this stream is used to feed one or more fermentation reactions. However, as would be apparent to one of skill in the art, CO may be produced elsewhere within the steel making process, and according to various embodiments of the invention, such alternative sources may be used instead of or in combination with exhaust gases from the BOF. Depending on the source (i.e., the particular stage within the steel making process), the CO content of the gases exhausted thereby may vary. Also, there may be periods when there are breaks in one or more of such streams, particularly in batch processing plants.

Typically, streams exhausted from the steel mill decarburisation process comprise a high concentration of CO and low concentrations of $H_2$. While such streams can be directly passed to the bioreactor with little or no further treatment, it may be desirable to optimise the composition of the substrate stream in order to achieve higher efficiency of alcohol production and/or overall carbon capture. For example, the concentration of $H_2$ in the substrate stream may be increased before the stream is passed to the bioreactor.

According to particular embodiments of the invention, streams from two or more sources can be combined and/or blended to produce a desirable and/or optimised substrate stream. For example, a stream comprising a high concentration of CO, such as the exhaust from a steel mill converter, can be combined with a stream comprising high concentrations of $H_2$, such as the off-gas from a steel mill coke oven.

An early stage of the steel making process typically involves the reduction of iron ore using coke. Coke is a solid carbon fuel source used to melt and reduce iron ore and is typically produced on-site at a steel mill. In the coke-making process, bituminous coal is fed into a series of ovens, which are sealed and heated at high temperatures in the absence of oxygen, typically in cycles lasting 14 to 36 hours. The solid carbon remaining in the oven is coke. It is taken to the quench tower, where it is cooled with a watery spray or by circulating an inert gas (nitrogen), then screened and sent to the blast furnace.

The volatile compounds produced during this process are generally processed to remove tar, ammonia, naphthalene, phenol, light oils and sulphur before the gas is used as fuel to heat ovens. Gas produced as a result of coke production typically has a high $H_2$ content (typical composition: 55% $H_2$, 25% $CH_4$, 6% CO, 3% $N_2$, 2% other hydrocarbons). As such, at least a portion of the coke oven gas may be diverted to the fermentation process for blending with a stream comprising CO, to improve alcohol productivity and/or overall carbon capture. It may be necessary to treat the coke oven gas prior to passing it to the fermenter to remove by-products that may be toxic to the culture.

Alternatively or additionally, an intermittent stream comprising CO, such as an exhaust stream from the converter, may be combined with and/or blended with a substantially continuous stream comprising CO and optionally $H_2$, such as syngas produced in a gasification process as described previously. In certain embodiments, this would maintain the provision of a substantially continuous substrate stream to the bioreactor. In a particular embodiment, the stream produced by the gasifier may be increased and/or decreased in accordance with the intermittent production of CO from an industrial source in order to maintain a substantially continuous substrate stream with a desirable or optimised composition. In another embodiment, the gasifier conditions may be altered as described previously in order to increase or decrease the $CO:H_2$ ratio, in accordance with the intermittent production of CO from an industrial source, in order to maintain a substantially continuous substrate stream with a desirable or optimised CO and $H_2$ composition.

Typically, the substrate streams used in the invention will be gaseous; however, the invention is not limited thereto. For example, the carbon monoxide may be provided to a bioreactor in a liquid. For example, a liquid may be saturated with a carbon monoxide containing gas and then that liquid added to a bioreactor. This may be achieved using standard methodology. By way of example, a microbubble dispersion generator (Hensirisak et al., Scale-up of microbubble dispersion generator for aerobic fermentation; Applied Biochemistry and Biotechnology Volume 101, Number 3, October, 2002) could be used for this purpose.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080, referred to above. The "Examples" herein provide other exemplary media.

The fermentation should desirably be carried out under appropriate conditions for the desired fermentation to occur (e.g. CO-to-alcohol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it may be preferable that the fermentation be performed at a pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, because a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

In particular embodiments, the microbial culture comprises acetogenic bacteria, such as *C. autoethanogenum*, that typically utilise a substrate comprising CO to produce products including acetate and/or ethanol. In such embodiments, the microbial culture may be grown under desirable conditions in a fermentation broth to promote growth and acetate production. The growth (or production) phase of acetogenic bacteria is typically associated with an increase in cellular matter (biomass accumulation) and acetate production, with little or no concomitant alcohol production. In particular embodiments of the invention, the microbial culture is perturbed such that acids present in the fermentation broth are converted to corresponding alcohols (e.g. acetate to ethanol and/or butyrate to butanol). Conversion of acids to alcohols can be referred to as the conversion phase.

In particular embodiments of the invention, the microbial culture can be perturbed such that acids produced by the culture during the production phase are converted to alcohols. In one embodiment of the invention the method is a batch-fed or continuous process which links production of a desired acid by microbial fermentation followed by use of that acid to produce its corresponding alcohol in accordance with the methods described herein before. In this embodiment, the method comprises at least the steps of a) in the primary bioreactor fermenting a substrate (preferably a substrate comprising carbon monoxide, more preferably a gaseous substrate comprising carbon monoxide) to produce one or more acids, b) in the secondary bioreactor culturing one or more strains of bacteria in the presence of a substrate comprising carbon monoxide, and c) introducing the one or more acids from (a) into the secondary bioreactor at a time when the one or more strains of bacteria are in a conversion phase to produce the alcohols corresponding to the one or more acids. In a related embodiment further growth reactors may feed bacteria to the primary and/or secondary bioreactors.

Whilst not wishing to be bound by any particular theory, it is considered that the conversion of acids to alcohols by acetogenic bacteria in accordance with the invention, such as *C. autoethanogenum*, occurs via a biochemical pathway involving the enzyme aldehyde oxido-reductase (AOR). AOR is a unique tungsten-containing enzyme able to reduce non-activated carboxylic acids to aldehydes. The aldehyde can be furthered reduced by aldehyde dehydrogenases to alcohol. AOR represents an important branch of the solventogenesis pathway. The tungsten cofactor has been shown to be crucial for enzyme activity. These enzymes can be found in fermentative microorganisms such as *Clostridium, Desulfitobacterium*, and *Pyrococcus*. The best characterized AORs belong to *Pyrococcus furiosus* whose genome contains five of which four have been characterized. The first AOR of *P. furiosus* has a broad substrate range but favours aldehydes derived from amino acids. Its crystal structure revealed the presence of a molybdopterin-based tungsten binding site. The second AOR, glyceraldehyde-3-phosphate ferredoxin oxidoreductase (GFOR), only utilizes glyceraldehydes-3-phosphate and the third AOR, formaldehyde ferredoxin oxidoreductase (FOR), prefers one to three carbon aldehydes. The fourth AOR, WOR5, has a broad substrate range. AOR have also been purified from *Clostridium formicoaceticum* and *thermoaceticum*. Product Recovery.

The products of the fermentation reaction can be recovered using known methods. Exemplary methods include those described in WO2007/117157, WO2008/115080 and U.S. Pat. Nos. 6,340,581, 6,136,577, 5,593,886, 5,807,722 and 5,821,111. However, briefly and by way of example only, ethanol may be recovered from the fermentation broth by methods such as fractional distillation or evaporation, and extractive fermentation.

Distillation of ethanol from a fermentation broth yields an azeotropic mixture of ethanol and water (i.e. 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. In this process, oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the non volatile oleyl alcohol is recovered for re-use in the fermentation.

Acetate may also be recovered from the fermentation broth using methods known in the art. For example, an adsorption system involving an activated charcoal filter may be used. In this case, microbial cells are typically first removed from the fermentation broth using a suitable separation method. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth be reduced to less than 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are known in the art and may be used in processes of the present invention. For example, U.S. Pat. Nos. 6,368,819 and 6,753,170 describe a solvent and cosolvent system that can be used for extraction of acetic acid from fermentation broths. As with the oleyl alcohol-based system described above for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms to extract the acetic acid. The solvent/co-solvent containing the acetic acid is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more products from the broth simultaneously or sequentially. Ethanol may conveniently be recovered by distillation, and acetate may be recovered by adsorption on activated charcoal, using the methods described above. The separated microbial cells can be returned to the fermentation bioreactor. The cell free permeate remaining after the ethanol and acetate have been removed can also be returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

$CO_2$ Removal

According to certain embodiments of the invention, the system used for $CO_2$ removal includes a means for selectively separating $CO_2$ from a mixed stream and a means for converting the $CO_2$ to products and/or preparing the $CO_2$ for storage or further use. Alternatively, the process includes a means for converting the $CO_2$ in a stream directly to products and/or substances suitable for storage or further use.

In one embodiment, $CO_2$ is selectively separated from a mixed gas stream using any separation means known in the art such as the exemplary methods provided below. Other methods of $CO_2$ separation that may be used in embodiments of the invention include extraction with a metal oxide, such as CaO, and use of porous carbon or selective solvent extraction such as amine extraction.

Amines such as aqueous monoethanolamine (MEA), diglycolamine (DGA), diethanolamine (DEA), diisopropanolamine (DTPA) and methyldiethanolamine (MDEA) are widely used industrially for removing $CO_2$ and hydrogen sulfide from natural gas streams and refinery process streams.

The $CO_2$ separated in such processes may be permanently stored. Many examples of permanent $CO_2$ storage are known in the art, such as geological storage (geo-sequestration), ocean storage and mineral storage (e.g. conversion to metal carbonates).

Geological storage involves injecting carbon dioxide, generally in supercritical form, directly into underground geological formations. Oil fields, gas fields, saline formations, unminable coal seams, and saline-filled basalt formations have been suggested as storage sites. Various physical (e.g., highly impermeable caprock) and geochemical trapping mechanisms can be used to prevent the $CO_2$ from escaping to the surface. For well-selected, designed and managed geological storage sites, the Intergovernmental Panel on Climate Change estimates that $CO_2$ could be trapped for millions of years, and the sites are likely to retain over 99% of the injected $CO_2$ over 1,000 years.

Several options for ocean storage have been proposed: (i) 'dissolution' injection of $CO_2$ by ship or pipeline into the water at depths of 1000 m or more, and the $CO_2$ subsequently dissolves; (ii) 'lake' deposition of $CO_2$ directly onto the sea floor at depths greater than 3000 m, where $CO_2$ is denser than water and is expected to form a 'lake' that would delay dissolution of $CO_2$ into the environment; (iii) conversion of the $CO_2$ to bicarbonates (using limestone); and (iv) storage of the $CO_2$ in solid clathrate hydrates already existing on the ocean floor, or use in growing more solid clathrate.

In mineral storage, $CO_2$ is exothermically reacted with abundantly available metal oxides to produce stable carbonates. This process occurs naturally over many years and is responsible for much of the surface limestone. The reaction rate can be made faster, for example by reacting at higher temperatures and/or pressures, or by pre-treatment of the minerals, although this method can require additional energy.

Alternatively, the separated $CO_2$ may be used to make products, such as direct or indirect conversion to hydrocarbons. A well-known process to produce a hydrocarbon is the process for making methanol from $CO_2$ and $H_2$. Catalytic or electrochemical dissociation of water to produce oxygen and hydrogen ions, wherein the hydrogen ions can be used to convert $CO_2$ to hydrocarbons is also known in the art. If $CO_2$ is heated to 2400° C., it splits into carbon monoxide and oxygen. The Fischer-Tropsch process can then be used to convert the CO into hydrocarbons. In such processes, the CO may be returned to the fermentation process. By way of example, the required temperature can be achieved by using a chamber containing a mirror to focus sunlight on the gas.

Alternatively, the separated $CO_2$ may be used in further fermentation(s) to produce products. Those skilled in the art will appreciate there are many examples of microbial fermentation reactions that convert $CO_2$ into products. For example, $CO_2$ may be converted into methane by anaerobic fermentation using methanogenic microbes. Examples of this and other related fermentation processes are disclosed in the aforementioned WO2006/108532. Further examples of fermentation reactions using $CO_2$ to produce products are provided in the aforementioned WO2007/117157 and WO2008/115080.

$CO_2$ is also a desirable feedstock in syngas production. $CO_2$ can be supplied to the reformer (gasifier) to reduce methane consumption and improve/increase the $H_2$:CO ratio. Accordingly, in one embodiment, at least a portion of the separated $CO_2$ may be supplied to a gasifier integrated into the fermentation process.

In another embodiment of the invention, the separated $CO_2$ may be converted to products such as concrete cement. In a process mimicking marine cement produced by coral when making their shells and reefs, magnesium and/or calcium can be combined with $CO_2$ to produce carbonates.

$CO_2$ is also readily absorbed by algae in a photosynthetic process, which can be used to capture carbon from waste streams. Algae rapidly grow in the presence of $CO_2$ and sunlight and can be harvested and converted into products such as biodiesel and/or alcohol.

Alternatively, the $CO_2$ may be directly captured from a stream without the need of an additional separation step. For example, in a particular embodiment, a stream, preferably a gaseous stream, comprising $CO_2$ may be passed through a second fermentation process to convert $CO_2$ to products.

Gas Separation

According to certain embodiments of the invention, the process used for gas separation comprises one or more steps of cryogenic fractionation, molecular sieving, adsorption, pressure swing adsorption, or absorption. Whatever process is used, gas separation can be performed to isolate at least a portion of one or more of the following components: $H_2$, $O_2$, $CO_2$ and CO, from the gas stream. Additionally or alternatively, gas separation according to embodiments of the invention may be used to remove one or more portions from the gas stream (e.g. $N_2$, $O_2$) so that the remainder may be more efficiently used, such as in the bioreactor.

Adsorption is the accumulation of gases, liquids or solutes on the surface of a solid or liquid. Absorption is the process by which one substance, such as a solid or liquid, takes up another substance, such as a liquid or gas, through minute pores or spaces between its molecules.

Pressure swing adsorption (PSA) is an adiabatic process which may be used for the purification of gases to remove accompanying impurities by adsorption through suitable adsorbents in fixed beds contained in pressure vessels under high pressure. Regeneration of adsorbents is accomplished by countercurrent depressurization and by purging at low pressure with previously recovered near product quality gas. To obtain a continuous flow of product, preferably at least two adsorbers are provided, such that at least one adsorber is receiving a gas stream (such as a waste/exhaust/biogas gas stream) and actually produces a product of desired purity. Simultaneously, the subsequent steps of depressurization, purging and repressurization back to the adsorption pressure are executed by the other adsorber(s). Common adsorbents may readily be selected by one of skill in the art dependent on the type of impurity to be adsorbed and removed. Suitable adsorbents include zeolitic molecular sieves, activated carbon, silica gel or activated alumina. Combinations of adsorbent beds may be used on top of one another, thereby dividing the adsorber contents into a number of distinct zones. Pressure swing adsorption involves a pendulating swing in parameters such as pressure, temperature, flow and composition of gaseous and adsorbed phase.

Purification or separation of gases using PSA normally takes place at near ambient feed gas temperatures, whereby the components to be removed are selectively adsorbed. Adsorption should ideally be sufficiently reversible to enable regeneration of adsorbents at similar ambient temperature. PSA may be used for treatment and/or purification of most common gases including CO, $CO_2$ and $H_2$. Examples of Pressure Swing Adsorption techniques are described in detail in Ruthven, Douglas M. et al., 1993 *Pressure Swing Adsorption*, John Wiley and Sons.

A molecular sieve is a material containing tiny pores of a precise and uniform size that is used as an adsorbent for gases and liquids. Molecules that are small enough to pass through the pores are adsorbed while larger molecules are not. A molecular sieve is similar to a common filter but operates on a molecular level. Molecular sieves often consist of aluminosilicate minerals, clays, porous glasses, microporous charcoals, zeolites, active carbons, or synthetic compounds that have open structures through which small molecules, such as nitrogen and water, can diffuse. Methods for regeneration of molecular sieves include pressure changing (e.g. in oxygen concentrators) and heating and purging with a carrier gas.

Membranes may be used, for example, to separate hydrogen from gases like nitrogen and methane, to recover hydrogen, to separate methane from biogas, or to remove water vapour, $CO_2$, $H_2S$ or volatile organic liquids. Different membranes, including porous and non-porous membranes, may be selected to serve the desired purpose as would be apparent to one of skill in the art upon consideration of the instant disclosure. For example, a Palladium membrane permits transport solely of $H_2$. In a particular embodiment, $CO_2$ can be separated from a stream, using a $CO_2$ permeable membrane. The $CO_2$ separated from the stream can be passed to a $CO_2$ remover such as the gasifier discussed previously.

Cryogenic fractionation involves compressing the gas stream and cooling it to a temperature low enough to allow separation by distillation. It may be used, for example, to remove $CO_2$. Certain components (e.g. water) are typically removed from the stream prior to performing cryogenic fractionation.

The same techniques can also be used to remove oxygen from a gaseous stream to produce CO and/or $CO_2$-rich anaerobic streams. In addition, oxygen can be removed biologically, by, for instance, passing the combustion exhaust gas into a sealed fermenter containing facultative aerobic micro-organisms, a reduced carbon substrate, and the necessary nutrients for the micro-organisms. The facultative aerobic micro-organisms can consume oxygen to create CO and/or $CO_2$-rich anaerobic streams.

Alternative methods for separating or removing $O_2$ from a gaseous stream are also well known in the art. However, by way of example, oxygen can be simply reduced and/or removed using hot copper or a catalytic converter.

Tailoring the gas separation process to a particular source of gas can make an otherwise non-commercially viable bioconversion process commercially viable. For example, with appropriate separation of CO from a car exhaust stream, a usable energy source may be obtained from the stream and unwanted gas emissions can be reduced. According to one embodiment of the invention, the gaseous substrate comprises Syngas containing CO and $H_2$, and gas separation is performed to remove hydrogen from the stream so that it may be isolated and used as a fuel outside of the fermentation process. The CO may be used to feed the fermentation reaction.

Intermittent Gas Streams

According to various aspects of the invention, the fermentation substrate is derived from an industrial source. Typically, substrates derived from industrial sources are gaseous and such gases may vary in composition and/or pressure and in some instances may be intermittent in nature. In certain embodiments, the invention provides means to improve or "smooth" supply of a gaseous substrate to a bioreactor for fermentation to produce products, particularly in instances where the substrate supply is intermittent or non-continuous in nature. Any known means for improving continuity or "smoothing" of a gaseous substrate stream may be used; however, particular embodiments of the invention include processes or systems that include at least one buffering means adapted to receive an intermittent substrate stream, and to deliver a substantially continuous substrate stream to a bioreactor.

In particular embodiments, the buffering means includes a storage tank adapted to receive intermittent gas streams. The intermittent stream may be compressed prior to entering the storage tank; alternatively, the storage tank may be configured to expand as it receives the substrate stream. For example, the buffer storage tank may include a 'floating roof' adapted to rise and fall to accommodate a gaseous substrate. Floating roof type storage tanks are known in the art, such as those used to accommodate supply and demand fluctuations in gas supply. The storage tank may be adapted to supply a substantially continuous substrate stream to a fermentation bioreactor, and as such may include a means for controlling the rate of flow of the stream exiting the tank.

In such embodiments, the storage tank serves as a substrate reservoir. However, according to an alternative embodiment, the buffer storage tank may be substituted by an alternative form of storage that performs the same function. For example, alternative forms may include one or more of absorption, adsorption, and pressure and/or temperature swings. Additionally or alternatively, the substrate may be dissolved in a liquid in the reservoir or held in a matrix, such as a porous solid material, until it is required. In particular embodiments of the invention, the substrate may be dissolved in a liquid in the storage tank and delivered directly to the bioreactor in solution when required.

Alternatively, the bioreactor itself may be configured such that the headspace above a fermentation liquid nutrient medium acts as a buffer for the intermittent stream. For example, the system may include a means to compress the gaseous substrate stream (when available) and pass it to the bioreactor. The pressure in the headspace in the bioreactor will increase when additional substrate is provided. The substrate is thus continuously available for conversion to products by microbial fermentation.

In another embodiment, the system may be adapted to receive gaseous substrate streams from multiple intermittent sources. Such a system may include means to combine and/or switch between streams to provide a substantially continuous substrate stream to the bioreactor.

Micro-organisms used in the fermentation reaction typically have an allowable temperature range, above or below which the reaction rate slows significantly. As such, the system may include cooling means, wherein when availability of the substrate stream is limited, the media in the bioreactor can be cooled to slow down the fermentation reaction and reduce demand for the substrate. Conversely, when the availability of the substrate stream increases, the temperature inside the bioreactor can be increased toward the upper end of the temperature range to increase the reaction rate.

Alternatively or additionally, a cooling means may be configured to even the cooling load so as to reduce the peak cooling load on a fermentation system. For example, assume that the cooling load required to cope with heat within a gas feed stream and/or a fermentation exotherm in a predetermined period (while gas is being processed) is 2 MW. To maintain the contents of the fermentation tank at a constant temperature during this period, heat must be removed at this rate to maintain a constant temperature within the tank. Conversely, during periods when there is no gas being processed and the exotherm essentially ceases, the cooling load will be zero. Thus, particularly for large-scale industrial applications, there will be periods when the cooling load is very high, which imposes significant constraints on the system. By levelling the cooling load, the maximum required cooling rate is reduced. Thus, it is possible to operate with a smaller scale cooling system, although on a continuous (or more continuous) basis.

Using the parameters of the previous example but assuming that the periods when gas is, and those when gas is not, processed are of equal duration, then heat may be removed from the fermentation tank continuously at 1 MW. Under these conditions, the heat removal rate when gas is being processed will not keep up with the heat input/generation, and the temperature within the fermentation tank will rise. When the gas is stopped, but cooling continues, the temperature within the fermentation tank will drop. In this way, a cooling system sized for 1 MW continuous load is required rather than a system sized for a 2 MW load that only runs half of the time. However, the temperature rise and subsequent drop must be limited to maintain the temperature inside the tank within the allowable range for the micro-organisms. Thus, according to particular embodiments, while not constant, the cooling load may be "smoothed," so that variations therein may be more gradual and/or more limited, in that there is a smaller difference between the maximum and minimum cooling loads.

Industrial Off Gas as a Resource for Fermentation

In accordance with other aspects of the invention, industrial waste gases are used in a fermentation reaction with no or only minimal additional scrubbing or pre-treatment steps being used to make the gases suitable therefor.

The waste gases may result from any number of industrial processes. The invention has particular applicability to supporting the production of ethanol from gaseous substrates such as high volume CO-containing industrial flue gases. Examples include gases produced during ferrous metal products manufacturing, non-ferrous products manufacturing, petroleum refining processes, gasification of coal, gasification of biomass, electric power production, carbon black production, ammonia production, methanol production and coke manufacturing. In a particular embodiment of the invention, the waste gases are generated during a process for making steel. For example, those skilled in the art will appreciate the waste gases produced during various stages of the steel making process have high CO and/or $CO_2$ concentrations. In particular, the waste gas produced during the decarburisation of steel in various methods of steel manufacturing, such as in an oxygen converter (e.g. BOF or KOBM), has a high CO content and low $O_2$ content making it a suitable substrate for anaerobic carboxydotrophic fermentation.

Waste gases produced during the carburisation of steel are optionally passed through water to remove particulate matter before passing to a waste stack or flue for directing the waste gas into the atmosphere. Typically, the gases are driven into the waste stack with one or more fans.

In particular embodiments of the invention, at least a portion of the waste gas produced during the decarburisation of steel is diverted to a fermentation system by suitable conduit means. By way of example, piping or other transfer means can be connected to the waste gas stack from a steel mill to divert at least a portion of the waste gas to a fermentation system. Again, one or more fans can be used to divert at least a portion of the waste gas into the fermentation system. In particular embodiments of the invention, the conduit means is adapted to provide at least a portion of the waste gas produced during the decarburisation of steel to a fermentation system. The control of and means for feeding gases to a bioreactor will be readily apparent to those of ordinary skill in the art to which the invention relates.

While steel mills can be adapted to substantially continuously produce steel and subsequently waste gases, particular aspects of the process may be intermittent. Typically the decarburisation of steel is a batch process lasting several minutes to several hours. As such, the conduit means may be adapted to divert at least a portion of the waste gas, such as the gas produced during the decarburisation of steel, to the fermentation system if it is determined the waste gas has a desirable composition.

The pH of the contents of the bioreactor used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilising *Clostridium autoethanogenum*, the pH may be adjusted to approximately 5.5 to 6.5, most preferably to approximately 5.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as $H_2SO_4$ can be used to raise and lower the pH of the fermentation medium and maintain the desired pH.

An additional benefit of the invention is that, because there is no or only minimal scrubbing and/or other treatment processes performed on the waste gases prior to their use in a fermentation reaction, the gases will contain additional material resulting from the industrial process, which additional material may be used, at least in part, as a feedstock for the fermentation reaction.

Blending of Streams

As noted previously, it may be desirable to blend an industrial waste stream with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

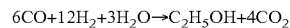
$$6CO + 12H_2 + 3H_2O \rightarrow C_2H_5OH + 4CO_2$$

However, in the presence of H2, the overall conversion is as follows:

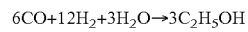
$$6CO + 12H_2 + 3H_2O \rightarrow 3C_2H_5OH$$

Accordingly, where industrial streams have a high CO content, but include minimal or no $H_2$, it may be desirable to blend one or more streams comprising $H_2$ with the waste stream comprising CO, prior to providing the blended substrate stream to the fermenter. The overall efficiency, alcohol productivity and/or overall carbon capture of the fermentation will be dependent on the stoichiometry of the CO and $H_2$ in the blended stream. However, in particular embodiments the blended stream may substantially comprise CO and $H_2$ in the following molar ratios: 20:1, 10:1, 5:1, 3:1, 2:1, 1:1 or 1:2.

In addition, it may be desirable to provide CO and $H_2$ in particular ratios at different stages of the fermentation. For example, substrate streams with a relatively high $H_2$ content (such as 1:2 CO:$H_2$) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the $H_2$ concentration may be greater or equal to zero).

Blending of streams may also have further advantages, particularly in instances where a waste stream comprising CO is intermittent in nature. For example, an intermittent waste stream comprising CO may be blended with a substantially continuous stream comprising CO and optionally $H_2$ and provided to the fermenter. In particular embodiments of the invention, the composition and flow rate of the substantially continuous stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the substrate stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas stream may be predominantly CO, and a secondary gas stream comprising a high concentration of $H_2$ may be blended to achieve a specified $H_2$:CO ratio. The composition and flow rate of the blended stream can be monitored by any means known in the art. The flow rate of the blended stream can be controlled independently of the blending operation; however the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of alcohol productivity and/or overall carbon capture.

It may not be possible or cost effective to provide CO and $H_2$ at a particular ratio all the time. As such, a system adapted to blend two or more streams as described above may be adapted to optimise the ratio with the available resources. For example, in instances where an inadequate supply of $H_2$ is available, the system may include means to divert excess CO away from the system in order to provide an optimised stream and achieve improved efficiency in alcohol production and/or overall carbon capture. In certain embodiments of the invention, the system is adapted to continuously monitor the flow rates and compositions of at least two streams and combine them to produce a single blended substrate stream of optimal composition, and means for passing the optimised substrate stream to the fermenter. In particular embodiments employing carboxydotrophic microbes to produce alcohol, the optimum composition of the substrate stream comprises at least 0% $H_2$ and up to about 1:2 CO:$H_2$.

By way of nonlimiting example, particular embodiments of the invention involve the utilisation of converter gas from the decarburisation of steel as a source of CO. Typically, such streams contain little or no $H_2$, therefore it may be desirable to combine the stream comprising CO with a stream comprising $H_2$ in order to achieve a more desirable CO:$H_2$ ratio. $H_2$ is often produced in large quantities at a steel mill in the coke oven. Accordingly, a waste stream from the coke oven comprising $H_2$ can be blended with a converter waste stream comprising CO to achieve a desirable composition.

Additionally, or alternatively, a gasifier may be provided to produce CO and $H_2$ from a variety of sources. The stream produced by the gasifier may be blended with a stream comprising CO to achieve a desirable composition. Those skilled in the art will appreciate that gasifier conditions can be controlled to achieve a particular CO:$H_2$ ratio. Furthermore, the gasifier may be ramped up and down to increase and decrease the flow rate of the stream comprising CO and $H_2$ produced by the gasifier. Accordingly, a stream from a gasifier may be blended with a substrate stream comprising CO to optimise the CO:$H_2$ ratio in order to increase alcohol productivity and/or overall carbon capture. Furthermore, the gasifier may be ramped up and down to provide a stream of varying flow and/or composition that may be blended with an intermittent stream comprising CO to achieve a substantially continuous stream of desirable composition.

Other sources of CO and/or $H_2$ that may be blended with a substrate stream comprising CO include reformation of hydrocarbons, such as natural gas and/or methane and reformation of methanol.

Embodiments of the invention are described above. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of $O_2$ that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired products) from particular stages, such as, for example, the bioreactor production stage (e.g. removal of ethanol by distillation).

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A process for maintaining stable fermentation of a gaseous substrate across multiple bioreactors, comprising:
   a. supplying a gaseous substrate to two or more primary bioreactors comprising a liquid nutrient media containing one or more microorganisms;
   b. fermenting the gaseous substrate in the two or more primary bioreactors to produce a fermentation broth comprising one or more microorganisms and one or more products;
   c. passing at least a portion of the fermentation broth from one primary bioreactor to one or more secondary bioreactors via a central bleed line; and
   d. determining whether one or more of the primary bioreactors of (c) is operational or not, wherein if one or more of the primary bioreactor is non-operational, at least a portion of fermentation broth from one or more operational primary bioreactors is provided to the one or more secondary bioreactors of (c) via the central bleed line.

2. The process of claim 1 wherein the primary bioreactors are operated at conditions to primarily promote microbial growth and the secondary bioreactors are operated at conditions to primarily produce one or more products.

3. A process for inoculating multiple bioreactors utilising a central bleed line, the process comprising:
   a. supplying a gaseous substrate to a first primary bioreactor comprising a liquid nutrient media;
   b. inoculating the first primary bioreactor with one or more microorganisms;
   c. fermenting the gaseous substrate to produce a fermentation broth comprising one or more microorganisms and one or more products;
   d. passing at least a portion of the fermentation broth from the first primary bioreactor via a central bleed line to inoculate more than one other primary bioreactors or secondary bioreactors at substantially the same time;
   e. operating the more than one other primary bioreactor at conditions to primarily promote microbial growth; and
   f. passing at least a portion of the fermentation broth from the more than one primary bioreactors at the same time via the central bleed line to inoculate one or more secondary bioreactors, the secondary bioreactors operated at conditions to primarily produce products.

4. A process for inoculating multiple bioreactors utilising a central bleed line, the process comprising:
   a. supplying a gaseous substrate to a first primary bioreactor comprising a liquid nutrient media;
   b. inoculating the first primary bioreactor with one or more microorganisms;
   c. fermenting the gaseous substrate to produce a fermentation broth comprising one or more microorganisms and one or more products;
   d. passing at least a portion of the fermentation broth from the first primary bioreactor via a central bleed line to inoculate at least one other primary bioreactor;
   e. operating the at least one other primary bioreactor at conditions to primarily promote microbial growth; and
   f. passing at least a portion of the fermentation broth from more than one primary bioreactors via the central bleed line to inoculate one or more secondary bioreactors at the same time, the secondary bioreactor operated at conditions to primarily produce products.

5. The process of claim 1 further comprising determining whether the supply of the gaseous substrate to the primary bioreactors or secondary bioreactors is limited, wherein if the supply of gaseous substrate is limited at least one primary bioreactor or secondary bioreactor is temporarily shut down until adequate supply of the gaseous substrate resumes.

6. The process of claim 1 further comprising substantially increasing the volume of fermentation broth in one or more operational primary bioreactors or one or more operational secondary bioreactors when at least one primary bioreactor or at least one secondary bioreactor becomes non-operational and diverting the gaseous substrate from the non-operational bioreactors to the operational bioreactor thereby maintaining steady product formation.

7. The process of claim 1, wherein the non-operational primary bioreactor of (d) is reinoculated by one or more operational primary bioreactors via the central bleed line.

8. The process of claim 1 wherein the product is selected from the group consisting of ethanol, 2,3-butanediol, acetate, and mixtures thereof.

9. The process of claim 1 wherein the microorganism is a carboxydotrophic bacterium selected from the group consisting of *Clostridium, Moorella, Oxobacter, Peptostreptococcus, Acetobacterium, Eubacterium* and *Butyribacterium*, or mixtures thereof.

10. The process of claim 1 wherein the gaseous substrate is selected from the group consisting of CO, $CO_2$, $H_2$, and mixtures thereof.

* * * * *